(12) United States Patent
Lewandowski et al.

(10) Patent No.: US 7,632,232 B2
(45) Date of Patent: Dec. 15, 2009

(54) ULTRASONIC DETECTION OF EAR DISORDERS

(75) Inventors: Jan Lewandowski, South Euclid, OH (US); Robert A. Bessler, Brownspoint, WA (US)

(73) Assignee: Otosonics Inc., Cleveland, OH (US)

(*) Notice: Subject to any disclaimer, the term of this patent is extended or adjusted under 35 U.S.C. 154(b) by 1043 days.

(21) Appl. No.: 10/729,199

(22) Filed: Dec. 5, 2003
(Under 37 CFR 1.47)

(65) Prior Publication Data

US 2004/0138561 A1 Jul. 15, 2004

Related U.S. Application Data

(60) Provisional application No. 60/442,869, filed on Jan. 27, 2003, provisional application No. 60/432,191, filed on Dec. 6, 2002.

(51) Int. Cl.
*A61B 8/00* (2006.01)
(52) U.S. Cl. ........................ 600/438; 600/437
(58) Field of Classification Search ................ 600/437, 600/438, 559; 73/585
See application file for complete search history.

(56) References Cited

U.S. PATENT DOCUMENTS

| | | | |
|---|---|---|---|
| 4,281,550 A * | 8/1981 | Erikson | 73/626 |
| 4,601,295 A * | 7/1986 | Teele | 600/559 |
| 4,691,714 A * | 9/1987 | Wong et al. | 600/551 |
| 5,546,956 A | 8/1996 | Thornton | |
| 5,622,172 A | 4/1997 | Li et al. | |
| 5,669,388 A | 9/1997 | Vilkomerson | |
| 5,699,809 A * | 12/1997 | Combs et al. | 600/558 |
| 5,735,282 A | 4/1998 | Hossack | |
| 5,921,928 A | 7/1999 | Greenleaf et al. | |
| 5,941,825 A | 8/1999 | Lang et al. | |
| 5,951,486 A | 9/1999 | Jenkins et al. | |
| 6,048,320 A * | 4/2000 | Brainard, II | 600/559 |
| 6,068,590 A | 5/2000 | Brisken | |
| 6,093,150 A | 7/2000 | Chandler et al. | |
| 6,102,860 A | 8/2000 | Mooney | |
| 6,126,614 A | 10/2000 | Jenkins et al. | |
| D439,335 S | 3/2001 | Walls et al. | |
| 6,390,975 B1 | 5/2002 | Walls et al. | |
| 6,398,736 B1 | 6/2002 | Seward | |
| 6,544,187 B2 | 4/2003 | Seward | |
| 6,631,287 B2 | 10/2003 | Newman et al. | |
| 7,131,946 B2 | 11/2006 | Lewandowski | |

(Continued)

FOREIGN PATENT DOCUMENTS

SU 1337052 A * 9/1987

OTHER PUBLICATIONS

Hormann, K. "Pathogenesis and pathophysiology of middle ear effusions", Abstract of Acta Otolaryngol. Suppl. 1987;440:pp. 1-59.*

(Continued)

*Primary Examiner*—Long V Le
*Assistant Examiner*—Jacqueline Cheng
(74) *Attorney, Agent, or Firm*—Pearne & Gordon LLP

(57) ABSTRACT

An apparatus and method for determining ear fluid viscosity. A transducer is operable to transceive a signal to interact with a fluid-containing portion of the ear. The viscosity of the fluid is determined using the transcieved signal.

11 Claims, 3 Drawing Sheets

U.S. PATENT DOCUMENTS

2003/0171655 A1 9/2003 Newman et al.
2003/0172734 A1* 9/2003 Greenwood .................. 73/597
2004/0167404 A1 8/2004 Bessler

OTHER PUBLICATIONS

Jung et al, Classification of Otitis Media and Surgical Principles, Sep. 6, 1999, Otolaryngologic Clinics of North America, vol. 32, issue 3, pp. 369-383.*

Takeuchi, Viscoelastic Properties Of Middle Ear Effusions From Pediatric Otitis Media With Effusion And Their Relation To Gross Appearance, 1990, European Archives of Oto-Rhino Laryngology, Issue 247, pp. 60-62.*

"Real-time B-scan Ultrasound in Middle Ear Assessment" A Preliminary Report, by Lynn S. Alvord, PhD, Perry G. Fine, MD, pp. 91-94, © 1990 by the American Institute of Ultrasound in Medicine.

"Ultrasonics in Otolaryngology", An Aid in the Disgnosis of Middle Ear Fluid, by David H. Abramson, MD, Allan L. Abramson, MD and D. Jackson Coleman, MD, New York, pp. 146-160, Arch Otolaryng, vol. 96, Aug. 1972.

"Uses of Ultrasound in Audiology", by Lynn S. Alvord, Journal of American Academy of Audiology, vol. 1, No. 4, pp. 227-235, Oct. 1990.

Preliminary Use of Endoluminal Ultrasonography in Assessment of Middle Ear with Effusion, by Chih-Hsiu Wu, MD, Chuan-Jen Hsu, MD, DMSc, Fon-Jou Hsieh, MD, American Institute of Ultrasound in Medicine, Journal vol. 17, pp. 427-430, dated 1998.

U.S. Appl. No, 10/729,741, filed Dec. 5, 2003, Lewandowski.

Christopher M. Discolo, Michael C. Byrd, Theresa Bates, Don Hazony, Jan Lewandowski and Peter J. Koltai, "Ultrasonic Detection of Middle Ear Effusion", American Medical Association, 2004, pp. 1407-1410.

Abramson, D.H. et al, "Ultrasonics in otolaryngology. An aid in the diagnostics of middle ear fluid", Archives of Otolaryngology, Aug. 1972, pp. 146-149, vol. 96, New York, USA.

Farmer-Fedor B. L. et al, "Acoustic intensity, impedance and reflection coefficient in the human ear canal", Journal of the Acoustical Society of America, Aug. 1, 2002, pp. 600-620, vol. 112, No. 2, AIP/Acoustical Society of America, Melville, New York, USA.

Saurav Paul et al, "Effects of middle ear fluid viscosity on reflectance tympanometry in chichillas", Feb. 2000, Retrieved from Internet: http://www.aro.org/archives/2000/5600.html, Retrieved Nov. 19, 2008.

Supplemental European Search Report dated Nov. 19, 2008.

* cited by examiner

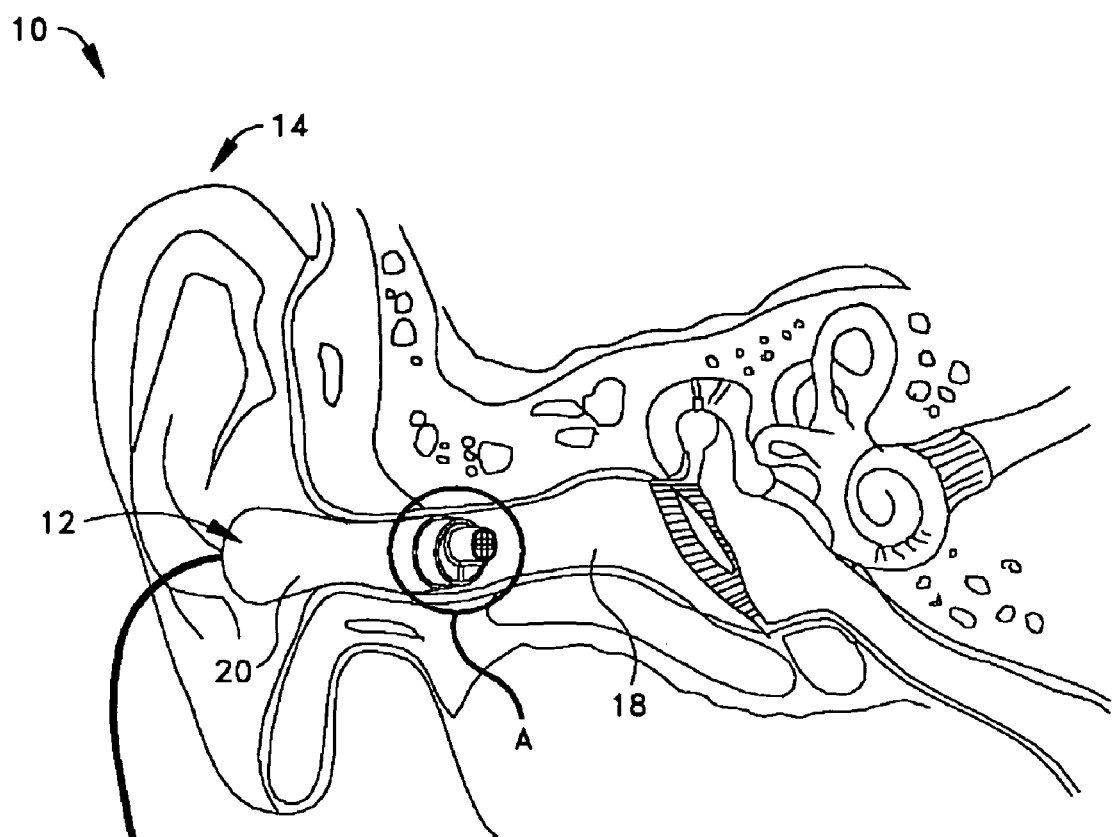
Fig.1
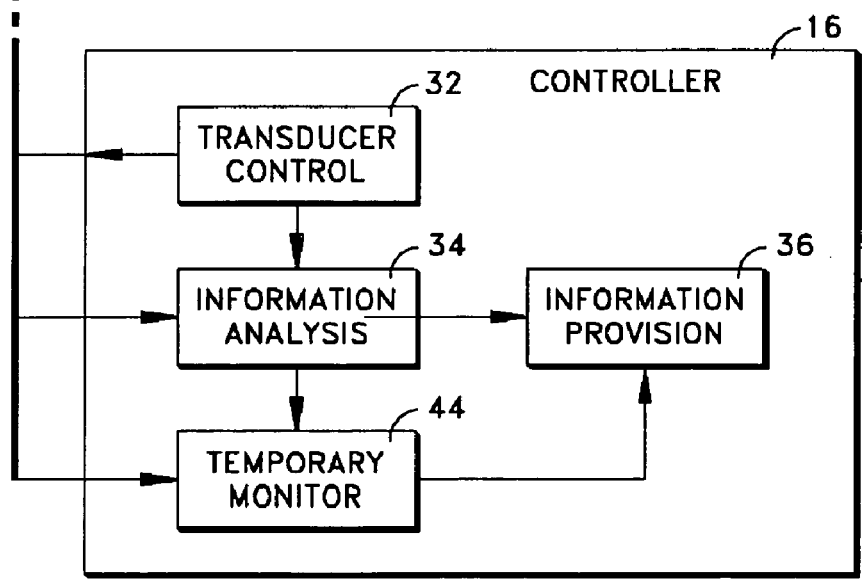

ULTRASONIC DETECTION OF EAR DISORDERS

RELATED APPLICATIONS

Benefit of prior Provisional Patent Application Ser. No. 60/432,191 and Provisional Patent Application Ser. No. 60/442,869 is hereby claimed, and the disclosures of these Provisional patent applications are expressly incorporated herein by reference.

FIELD OF THE INVENTION

The present invention relates to detection of at least one ear disorder. More particularly, the present invention relates to an apparatus and method utilizing viscosity of fluid within the ear.

BACKGROUND OF THE INVENTION

Ear disorders are common afflictions affecting many people. For example, otitis media (OM), an inflammatory process of the middle ear, is the most common clinical condition seen by pediatricians in children 15 years old and younger. OM is characterized by the presence of middle ear effusion (MEE), a middle ear infection. Complications of undiagnosed OM can include hearing loss and consequently delay in the development of speech and language skills. The combination of the gravity of the complications of undiagnosed OM and an unsatisfactory, noninvasive diagnostic technique often leads to unnecessary over medication of children with antibiotics.

The most reliable determination of the presence of MEE is direct surgical exploration (myringotomy). This is accomplished by making a small incision in the tympanic membrane followed by fluid aspiration. It is an invasive procedure and must be performed in a surgical setting under anesthesia. None of the existing non-invasive methods for determining the presence of MEE achieve 100% agreement with myringotomy. In order to reduce unnecessary antibiotic use and assuring at the same time effective and complication-free treatment of patients with OM, there is an urgent need to develop a simple but more accurate method for non-invasive method for MEE detection.

BRIEF SUMMARY OF THE INVENTION

In accordance with one aspect, the present invention provides an apparatus for determining ear fluid viscosity. The apparatus includes a transducer operable to transceive a signal to interact with a fluid-containing portion of the ear. The apparatus also includes means for determining the viscosity of the fluid using the transcieved signal.

In accordance with another aspect, the present invention provides a method of determining ear fluid viscosity. A transducer is operated to transceive a signal that interacts with a portion of an ear that contains fluid. A viscosity of the fluid is determined using the transcieved signal.

BRIEF DESCRIPTION OF THE DRAWINGS

FIG. 1 is a schematic and pictorial view of an example apparatus interacting with an ear in accordance with the present invention;

DESCRIPTION OF EXAMPLE EMBODIMENTS

Figure 2:
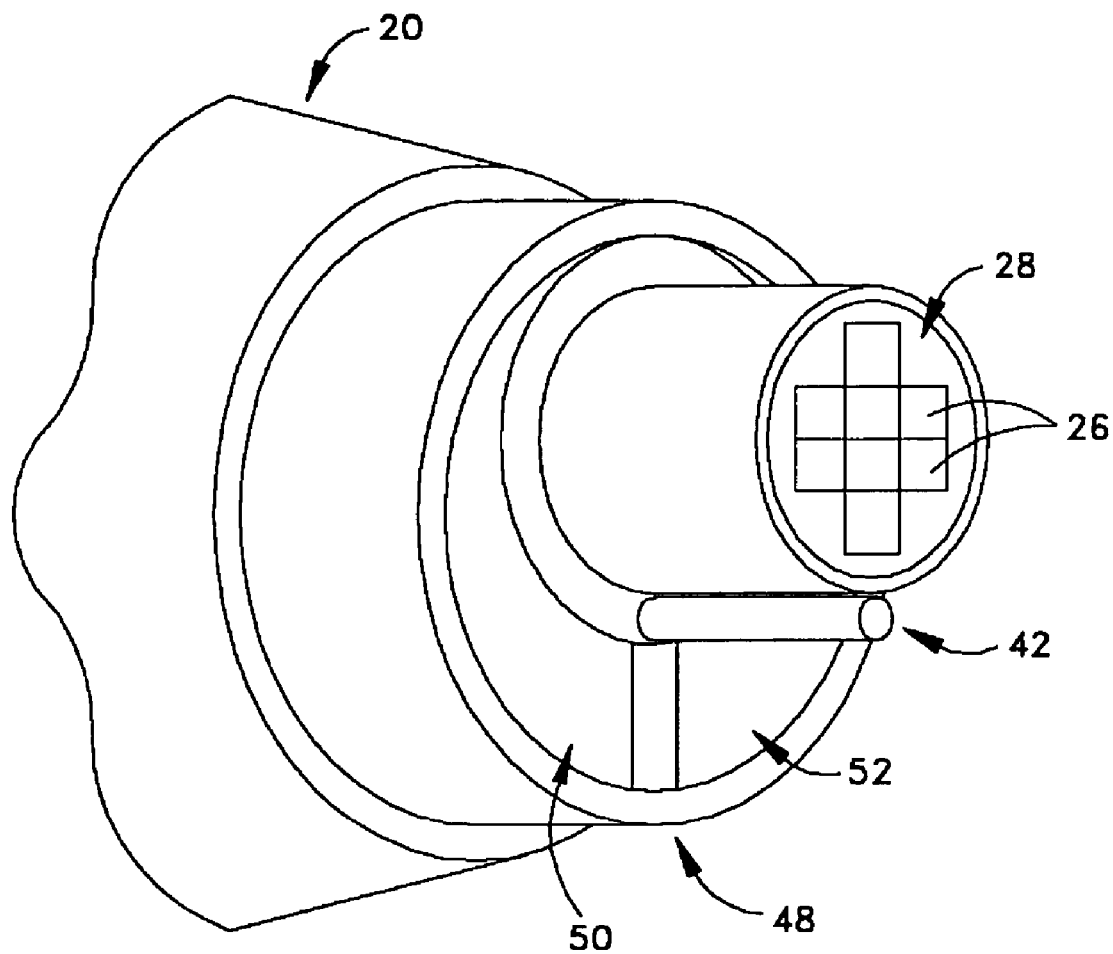
FIG. 2 is a partially schematic enlarged view of area A of FIG. 1 and shows details of one example of an array of transducers for the apparatus of FIG. 1 along with other components.

An example of an apparatus 10 for the detection of ear disorders, such as middle ear effusion (MEE), etc., in accordance with the present invention, is shown in FIG. 1. The apparatus 10 includes a probe 12 that interacts with an ear 14. The apparatus 10 also includes structure 16 (e.g., components) for operation control, information analysis, information provision to a user (e.g., a medical examiner) of the apparatus, and possibly other functions.

The structure 16 associated with the control, analysis, provision, etc. is schematically shown in FIG. 1. Hereinafter, the schematically shown structure 16 is referred to as a controller 16, with an understanding that multiple functions can be performed by the controller. It is to be understood that the controller 16 can have a variety of designs, configurations, etc. Further, it is to be understood that specifics concerning the controller 16 are not intended to be limitations on the present invention. Any structure and/or configuration capable of performing the functions described herein may be utilized. Such variation of the structure is intended to be within the scope of the present invention.

Turning to the probe 12, the probe interacts with the ear 14 and may be inserted into (e.g., penetrate into the space of) a canal 18 of the ear. A conformable sleeve 20 may be provided to encapsulate all or a substantial portion of the probe 12. The sleeve 20 provides conformability and comfort, and helps enable the probe 12 to be useable with a variety of ear sizes. The sleeve 20 may be made of any material suitable to allow such conformability and comfort, such as silicone or polyurethane elastomers.

In one example, the probe 12 (FIG. 2) includes a plurality of sensors 26 supported thereon. In one preferred example, the sensors 26 are transducers 26. Also, in one specific example, the transducers 26 are ultrasonic transducers. Any number of transducers 26 may be utilized.

Each transducer is able to transceive an ultrasonic signal (e.g., a wave beam). Specifically, each transducer is able to transmit an ultrasonic signal and is able to receive the ultrasonic signal that is reflected back to the transducer. For each transducer, the output of an ultrasonic signal is in response to an electrical stimulus signal, and the receipt of the reflected signal results in a return electrical signal. The operation of each transducer to output the associated signal can be referred to as "firing."

In one example, each transducer has a center frequency in the range of 1-60 MHz (i.e., the output signal has such a frequency). The transducers 22 may be made from known materials and by known methods. However, newly developed materials and methods may be used.

Each reflected signal that is received conveys information (e.g., data) concerning the surface from which the signal was reflected. Upon interaction of the probe 12, having the included transducers 26, with the ear 14 (FIG. 1), the signals are reflected from surfaces within the ear. For example the signals may reflect from the tympanic membrane within the ear 14. As an example of the information conveyed via the reflected signal, amplitude of the reflected signal can be used to predict a fluid state within a middle ear portion of the ear 14. Such fluid state within the middle ear can be associated with an ear disorder. In the case of effusion, a second echo reflected from the middle ear cavity provides information concerning an ear disorder.

The transducers 26 (FIG. 2) on the probe 12 are arranged in an array 28. Within the present example, the array has an outer diameter of less than 5 mm. Each transducer within the array 28 is oriented along a different direction. Specifically, each transducer is oriented such that the associated signal is output along a direction that is different from directions associated with the other transducers. As a corollary, the receipt of the reflected signal back to each transducer is generally along the same direction. The output and receipt of a signal along a direction can be thought of as "aiming" the signal along a beam angle. It is to be appreciated that all constructions and/or methodologies for directing the signals are intended to be within the scope of the present invention.

Figure 3:
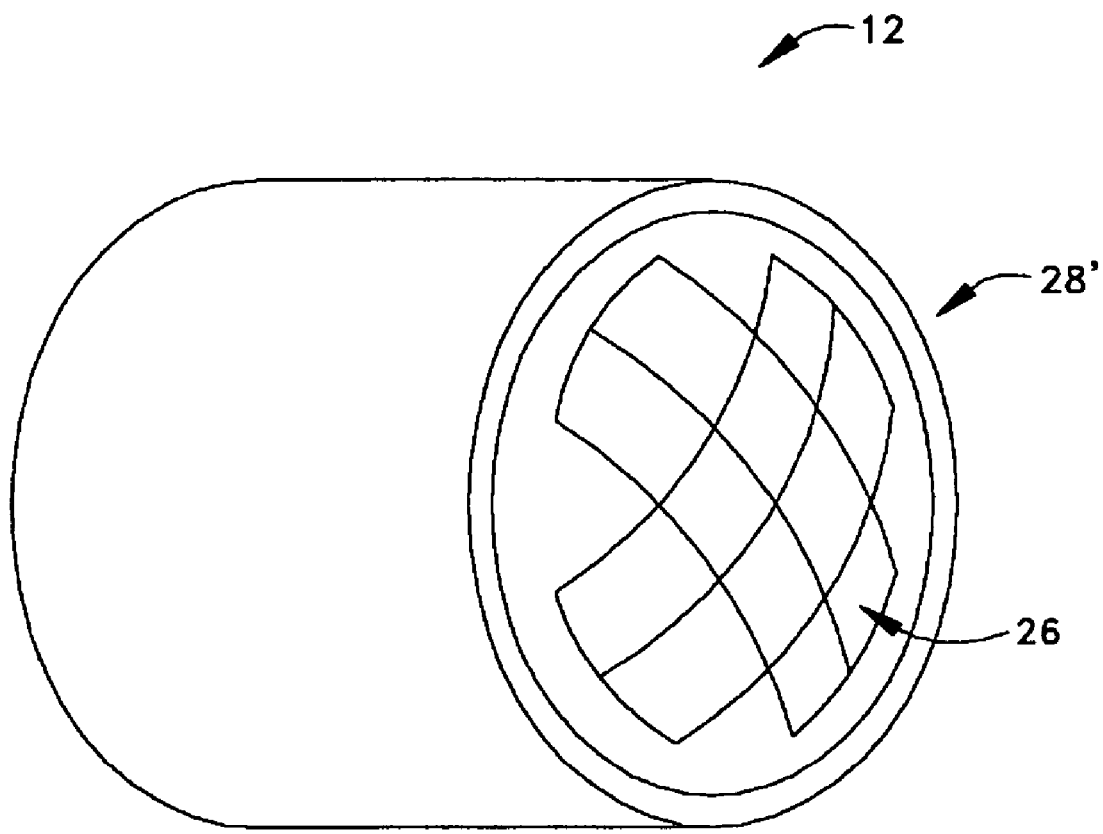
FIG. 3 is a partially schematic enlarged view of a curved array of transducers for the apparatus of FIG. 1.

In one example, which is shown in the FIG. 3, the orientation includes placement of the transducers 26 in a curved array 28' on the probe 12. Specifically, the transducers 22 are placed on a semispherical end surface portion of the probe 12. Alternatively, the transducers 22 may be arranged in some other non-planar fashion, with some means (e.g., varied orientation) to provide the differing direction. However, the curved array 28' arrangement provides a readily obtainable effect of each transducer being aimed at a different beam angle.

Only ultrasonic signals (e.g., beams) originating from certain beam angles will produce useful data. Therefore, the orientation along different directions (e.g., curved array 28') of transducers 22 ensures that an ideal beam angle will be present and will generate useful data.

Further, the transducers 22 may be operated (e.g., "fired") sequentially, rather than simultaneously. By firing sequentially, it can be determined which transducer is positioned at a most useful beam angle. In order to obtain the most accurate determination concerning ear disorder detection, the only data used is from the transducer determined to be at the most useful angle.

Turning to the controller 16 (FIG. 1), the controller includes a portion 32 for controlling operation of the transducers 26. In one example, the firing of each transducer is accomplished via the transducer control portion 32 providing the electrical stimulus signal to the respective transducer. The controller 16 also receives the return electrical signals upon receipt of the return ultrasonic signals at the transducers 26. Within the one example, the control of operation by the transducer control portion 32 is such that the transducers 26 are sequentially fired.

The controller 16 includes a portion 34 for analyzing the information conveyed within the reflected signal (e.g., one or more characteristics of the reflected signal) and transmitted to the controller via the electrical return signal. As one example, the information analysis portion 34 can analyze the reflected signal amplitude.

Also, the controller 16 includes a portion 36 for providing analysis information to the user of the apparatus 10. The information provision portion 36 may include a display 36 from which the user may discern the information.

The information analysis portion uses the signal information to determine if an ear disorder exists. Specifically, in accordance with the present invention, the analysis provides a determination of viscosity of the fluid within the ear. The viscosity is related to the presence of an ear disorder.

In one example, only the signal from only one transducer is used to determine an accurate indication for the ear disorder detection. The utilized signal is based upon selection of a transducer that provides the best indication. The best indication is logically the transducer that is directed toward a certain portion of the ear for reflection therefrom. In one example, the certain portion is the tympanic membrane. Fluid within the middle ear is located behind the tympanic membrane. As such, the information analysis portion 34 determines which transducer is directed at the certain ear portion (i.e., the tympanic membrane) via signal analysis.

The signal analysis can be made easy via control the transducers to operate sequentially. The use of a sequential operation approach allows analysis without conflict from other signals. The transducer control portion 32 and the information analysis portion 34 of the controller 16 can thus interact and cooperate to accomplish this feature. However, it is to be appreciated that certain aspects of the present invention may not be limited to single transducer signal use for disorder determination and/or sequential operation.

It should be noted that the above-discussed examples include plural transducers. It is to be understood that the present invention is not limited to the use of a plurality of transducers, but can be carried out using only a single transducer. Within such a single transducer apparatus, it should be understood that one or more changes from the example discussed above and shown in the drawings will exist. For example, the probe will only contain a single transducer. Further, the components of the controller 16 that deal with use and control of plural transducers will be modified of obviated.

Turning to other aspects, one specific example of the apparatus 10 may include a temperature sensing means 42 (FIG. 2) that is operatively connected to a temperature monitoring portion 44 (FIG. 1) of the controller 16. The temperature sensing means 42 may be attached to or integrated with the probe 12 so that temperature measurements of the ear 14 may be taken in connection with operation of the transducer array 28. The temperature sensing means 42 may be, for example, a thermometer or other suitable device known in the art. The monitoring portion 44 is operatively connected to the information provision portion 36 such that the temperature information is also provided to the user.

Another specific example of the apparatus 10 may include a fluid delivery system 48 (FIG. 2) for delivering and removing ultrasound transmitting medium to and from the canal 18 (FIG. 1) of the ear 14. The ultrasound transmitting medium may, inter alia, aid in acoustic coupling between the ear 14 and the transducers 26 and may comprise, for example, water, saline, commercially available known mediums, such as AYR-SALINE, NASAL-GEL or VO-SOL, etc. As shown in the Example of FIG. 2, the fluid delivery system 48 may be included within the probe 12. Such an example of the fluid delivery system 48 may include an ultrasound transmitting medium outlet 50 and an ultrasound transmitting medium inlet 52. The outlet 50 provides a conduit by which ultrasound transmitting medium may be delivered to the ear 14 and into the ear canal 18. The inlet 52 provides an evacuation component by which the ultrasound transmitting medium may be removed from the ear 14. The outlet 50 and inlet 52 may be connected, for example, by flexible tubing to external devices, such as a reservoir for containing the ultrasound transmitting medium. The use of flexible tubing may be advantageous in examinations involving pediatric patients because such flexible tubing permits the patient to retain movement of the head during data acquisition.

It is to be appreciated that the apparatus 10 may have any suitable configuration, set-up, etc. In FIG. 1, shown components of the controller, (e.g., the transducer control portion 32, the information analysis portion 34, and the information provision portion 36) are schematically depicted as being separate from the probe. However, it is to be understood that the apparatus 10 may be embodied in other suitable forms, such as a self-contained hand-held unit that directly incorporates such components as the transducer control portion 32, the information analysis portion 34, and the information provision portion 36. Also, the apparatus 10 may include additional components.

As another aspect of the present invention, one or more ear disorders are detected by a method. In one example, the method includes the steps of providing a probe that includes a plurality of transducers, interacting the probe with an ear, operating the plurality of transducers to provide information, and determining the existence of an ear disorder using the information. In another example, the method includes providing the probe 12, which includes the plurality of transducers 26 (e.g., arranged in a curved array 28'). The probe 12 is interacted with the ear 14, and the existence of an ear disorder is determined. The method may further include any of the following steps: sequentially firing the transducers 26, inserting into the ear canal 18, providing an ultrasound transmitting medium to the ear, evacuating the ultrasound transmitting medium from the ear canal, and/or measuring the temperature of the ear 14. Further, it is contemplated that this method can be performed within a relatively short time period (e.g., 60 seconds or less).

It is to be appreciated that the present invention provides ultrasonic detection of ear disorders. As such, the present invention provides a method and apparatus 10 for the investigation of the viscous state of fluid in an ear. The fluid in an ear may be described as serous (thin), purulent (medium), or mucoid (thick). Via one embodiment of the present invention, the apparatus 10 is able to distinguish whether the fluid in the ear is serous, purulent or mucoid. It has been found that pulse echo amplitudes can be used to predict the fluid state. For example, the first and second pulse amplitudes can be used to identify the mucoid state of the fluid. For a further example, a binary logic regression model fitted to the mucoid (yes/no) response as a function of the first and second pulse amplitude was able to correctly distinguish the yes/no mucoid states of all possible experimental yes/no pairings with a high accuracy, such as 100% accuracy.

An example of the methodology and observations therefrom regarding the investigation of the viscous state of fluid in an ear will now be discussed. Concentration of mucin was determined as a significant factor determining viscosity of effusion. Artificial effusion was prepared from porcine stomach mucin (Sigma) dissolved in phosphate buffered saline (PBS). A series of "artificial MEE" solutions with concentrations between 0 and 10% (w/v) of mucin were tested.

Viscosities of the solutions were measured using Cannon-Fenske type capillary viscometers. Type A viscometer was used for measurements at low viscosity solutions, type B for middle range and type C for high viscosity range. Measurements were done in a thermostatically controlled cell at 25° C. Viscosities of tested solutions were calculated using capillary constants values from manufacturer provided calibration certificates. A series of "artificial MEE" solutions with concentrations between 0 to 10% (w/v) of mucin were prepared.

Correlation between viscosity of fluid and amplitude has logarithmic character, i.e., higher sensitivity to viscosity changes in the low viscosity range. This relation may be favorable for the present invention because there is likely a rather small viscosity difference between serous and purulent effusion, which are in the low viscosity range. Viscosity of mucoid fluid is likely significantly higher than either of serous of purulent so even if it falls into the lower sensitivity part of the curve it remains detectable. Tested viscosity range of kinematic viscosity was between 0.98 cSt (PBS) and 168 cSt (10% mucin solution in PBS).

As the ultrasonic signal propagates through the medium, the energy of the signal is absorbed and therefore the intensity decreases with the distance. The decrease of peak pressure with distance is described by the equation:

$$p(x) = p_o \exp(-\alpha x)$$

wherein x is distance, $\alpha$ is the attenuation coefficient of the medium, and $p_o$ is pressure at x=0.

The attenuation coefficient $\alpha$ depends on the frequency of the signal. In the case of Newtonian fluids, $\alpha$ is proportional to the second power of frequency.

Attenuation of the ultrasonic signal traveling through the medium can be expressed as the energy loss of the signal per unit distance. An ultrasonic signal traveling though different layers of tissue also loses energy due to the reflections from the interfaces between sections having different values of characteristic impedance. The energy loss of the traveling signal is due to reflection and can be distinguished from the energy loss due to attenuation since reflection coefficients are frequency independent.

The coefficient of attenuation, $\alpha$, however, depends on the signal frequency as described by equation:

$$\alpha(f) = \alpha_o f^n$$

where $\alpha$ is the frequency dependent attenuation coefficient of the medium, f is the signal frequency, and n and $\alpha_o$ are attenuation coefficients characteristic to the medium. For Newtonian fluids, n=2.

Viscosity of MEE changes at different stages of the disease from low (purulent effusion) to high (mucoid) with intermediary serous effusion. While low viscosity purulent fluid indicates AOM with high chance of clearing without surgical intervention, presence of high viscosity mucoid fluid may be the indication for tube placement.

The energy of the ultrasonic signal traveling through the middle ear is attenuated by the effusion according to the above equation. In consequence, the amplitude is related to the viscosity of the effusion and the width of the middle ear. The width can be calculated from the delay of the membrane echo and middle ear echo.

In summary, it is to be appreciated that the present invention can provide for MEE detection by analysis of ultrasonic signals generated from miniature transducers arranged in a curved array. The MEE detection may be non-invasive and may be performed on a conscious patient without the need for anesthesia. The ultrasonic detection of MEE is based on the analysis of the ultrasonic signal reflected (e.g., an echo) from the tympanic membrane and, in the case of effusion, a second echo reflected from the middle ear cavity. In the case of a normal ear, a significant portion of the ultrasonic signal energy is reflected due to the mismatch between acoustic impedance of the tympanic membrane and the impedance of air filling the middle ear cavity. When the effusion is present, the energy of a reflected pulse is significantly lower. This is due to the good match of impedances of the tympanic membrane and the fluid, which allows the pulse to penetrate into the middle ear cavity.

It should be evident that this disclosure is by way of example and that various changes may be made by adding, modifying or eliminating details without departing from the fair scope of teaching contained in this disclosure. In particular, the discussion, equations and methodology presented herein is by way of example only and other variations are contemplated and considered within the scope of the invention.

The invention claimed is:

1. A method for testing for otitis media, comprising the steps of:

positioning an ultrasound probe at a location spaced away from a tympanic membrane of a human patient;

using the ultrasound probe to detect the presence and measure the viscosity of a middle ear effusion in the human patient while the ultrasound probe is positioned at the location spaced away from the tympanic membrane, wherein the viscosity of the middle ear effusion is measured based on an analysis of a first pulse echo reflected from the tympanic membrane and a second pulse echo reflected from a middle ear cavity of the human patient; and comparing the measured viscosity of the middle ear effusion in the human patient with at least three predetermined values for effusion viscosity, wherein such comparison provides information regarding the likelihood of presence of bacterial infection in the middle ear effusion in the human patient.

2. The method for testing of claim 1 wherein each of said predetermined values is based on a plurality of predetermined ranges of fluid viscosity measurements.

3. The method of claim 1, wherein the ultrasonic probe contains a plurality of transducers that are each adapted to transceive an ultrasonic signal.

4. A method for determining if a human patient is a candidate for receiving antibiotic treatment, wherein the presence of a middle ear effusion in the patient is detected by an ultrasound probe that is positioned at a location spaced away from a tympanic membrane of the human patient and the viscosity of the middle ear effusion is determined based on an analysis of a first pulse echo reflected from the tympanic membrane and a second pulse echo reflected from a middle ear cavity of the human patient, and comparing the determined viscosity of the middle ear effusion with at least one predetermined fluid viscosity value.

5. The method of claim 4, wherein the ultrasonic probe contains a plurality of transducers that are each adapted to transceive an ultrasonic signal.

6. An apparatus for determining the viscosity of a fluid in a middle ear cavity, the apparatus including:

a plurality of transducers that are each adapted to transceive an ultrasonic signal to interact with a tympanic membrane and the middle ear cavity, wherein the apparatus is configured to use pulse echo amplitudes to determine whether the fluid in the middle ear cavity is serous, purulent or mucoid while the plurality of transducers are positioned at a location spaced away from the tympanic membrane, wherein the apparatus is configured to determine the viscosity of the fluid in the middle ear cavity by an analysis of pulse echo amplitudes, measured by at least one of the plurality of transducers, of a first pulse echo reflected from the tympanic membrane and a second pulse echo reflected from the middle ear cavity.

7. The apparatus of claim 6, wherein the plurality of transducers are arranged in a curved array.

8. A method of determining the viscosity of a fluid in a middle ear cavity, the method including:

positioning a plurality of transducers at a location spaced away from a tympanic membrane;

operating a plurality of transducers while the plurality of transducers are positioned at the location spaced away from the tympanic membrane, wherein the viscosity of the fluid in the middle ear cavity is measured based on an analysis of a first pulse echo reflected from the tympanic membrane and a second pulse echo reflected from the middle ear cavity; and using amplitudes from the first pulse echo and the second pulse echo to determine whether the fluid in the middle ear cavity is serous, purulent or mucoid.

9. The method of claim 8, wherein the plurality of transducers are operated sequentially.

10. The method of claim 8, wherein the plurality of transducers are operated simultaneously.

11. The method of claim 8, wherein the plurality of transducers is are each adapted to transceive an ultrasonic signal.

* * * * *

UNITED STATES PATENT AND TRADEMARK OFFICE
CERTIFICATE OF CORRECTION

PATENT NO. : 7,632,232 B2 Page 1 of 1
APPLICATION NO. : 10/729199
DATED : December 15, 2009
INVENTOR(S) : Lewandowski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1711 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,632,232 B2 | Page 1 of 1 |
| APPLICATION NO. | : 10/729199 | |
| DATED | : December 15, 2009 | |
| INVENTOR(S) | : Lewandowski et al. | |

It is certified that error appears in the above-identified patent and that said Letters Patent is hereby corrected as shown below:

Title Page, Item (56)

In the "Other Publications" section, please add the following reference: -International Search Report from PCT/US03/38768, dated July 8, 2004-

In the claims, column 8, line 36, please delete the word "is"

Signed and Sealed this
Third Day of January, 2012

David J. Kappos
*Director of the United States Patent and Trademark Office*